US00PP16039P2

(12) United States Plant Patent
Hoogendoorn

(10) Patent No.: US PP16,039 P2
(45) Date of Patent: Oct. 18, 2005

(54) ***ALSTROEMERIA* PLANT NAMED 'ZAPRIJUL'**

(50) Latin Name: *Alstroemeria hybrida*
Varietal Denomination: Zaprijul

(75) Inventor: Cornelis Arie Hoogendoorn, Rijsenhout (NL)

(73) Assignee: Van Zanten Plants B.V., Hillegom (NL)

( * ) Notice: Subject to any disclaimer, the term of this patent is extended or adjusted under 35 U.S.C. 154(b) by 250 days.

(21) Appl. No.: 10/437,948

(22) Filed: May 13, 2003

(51) Int. Cl.[7] ..... A01H 5/00
(52) U.S. Cl. ..... Plt./309
(58) Field of Search ..... Plt./309

*Primary Examiner*—Kent Bell
(74) *Attorney, Agent, or Firm*—C. A. Whealy

(57) ABSTRACT

A new and distinct cultivar of *Alstroemeria* plant named 'Zaprijul', characterized by its compact, upright and outwardly spreading plant habit; purple and violet bi-colored flowers with dark purple-colored spots and stripes; and excellent postproduction longevity.

1 Drawing Sheet

Botanical classification/cultivar designation: *Alstroemeria hybrida* cultivar Zaprijul.

BACKGROUND OF THE INVENTION

The present Invention relates to a new and distinct cultivar of *Alstroemeria* plant, botanically known as *Alstroemeria hybrida*, commercially used as a pot-type flowering *Alstroemeria*, and hereinafter referred to by the name 'Zaprijul'.

The new Alstroemeria is a product of a planned breeding program conducted by the Inventor in Rijsenhout, The Netherlands. The objective of the breeding program was to develop new compact container *Alstroemeria* cultivars with desirable flower and plant qualities, attractive flower colors and excellent postproduction longevity.

The new *Alstroemeria* originated from a cross made by the Inventor in 1997 in Rijnsburg, The Netherlands, of a proprietary *Alstroemeria hybrida* selection identified as 94186-002PN, not patented, as the female, or seed, parent with a proprietary *Alstroemeria hybrida* selection identified as 96123-001PN, not patented, as the male, or pollen, parent. The new *Alstroemeria* was discovered and selected by the Inventor as a flowering plant within the progeny of the stated cross in a controlled environment in Rijnsburg, The Netherlands in May, 1998.

Asexual reproduction of the new cultivar by root divisions taken in a controlled environment in Rijsenhout, The Netherlands, since May, 1998, has shown that the unique features of this new *Alstroemeria* are stable and reproduced true to type in successive generations of asexual propagation.

SUMMARY OF THE INVENTION

Plants of the cultivar Zaprijul have not been observed under all possible environmental conditions. The phenotype may vary somewhat with variations in environment such as temperature and light intensity without, however, any variance in genotype.

The following traits have been repeatedly observed and are determined to be the unique characteristics of 'Zaprijul'.

These characteristics in combination distinguish 'Zaprijul' as a new and distinct cultivar:

1. Compact, upright and outwardly spreading plant habit.
2. Purple and violet bi-colored flowers with dark purple-colored spots and stripes.
3. Excellent postproduction longevity.

Plants of the new *Alstroemeria* can be compared to plants of the parent selections. Plants of the new *Alstroemeria* differ from plants of the parent selections in flower coloration as plants of the female parent selection have pink-colored flowers and plants of the male parent selection have lilac-colored flowers.

Plants of the new *Alstroemeria* can be compared to plants of the cultivar Staprilene, disclosed in U.S. Plant Pat. No. 11,683. In side-by-side comparisons conducted in Rijsenhout, The Netherlands, plants of the new *Alstroemeria* differed from plants of the cultivar Staprilene in the following characteristics:

1. Plants of the new *Alstroemeria* had longer lateral branches than plants of the cultivar Staprilene.
2. Plants of the new *Alstroemeria* had shorter leaves than plants of the cultivar Staprilene.
3. Plants of the new *Alstroemeria* had purple and violet bi-colored flowers whereas plants of the cultivar Staprilene had yellow and white bi-colored flowers.

BRIEF DESCRIPTION OF THE PHOTOGRAPH

The accompanying colored photograph illustrates the overall appearance of the new *Alstroemeria*, showing the colors as true as it is reasonably possible to obtain in colored reproductions of this type. Colors in the photograph may differ slightly from the color values cited in the detailed botanical description which accurately describe the colors of the new *Alstroemeria*.

The photograph comprises a side perspective view of a typical flowering plant of 'Zaprijul'.

DETAILED BOTANICAL DESCRIPTION

The aforementioned photograph, following observations and measurements describe plants of the new *Alstroemeria* grown in Rijsenhout, The Netherlands in a glass-covered greenhouse in 17-cm containers. During the production of the plants, day temperatures ranged from 15 to 25° C. and night temperatures ranged from 10 to 15° C. Plants used for the photograph and description were about four months old. The photograph and the description were taken during August and September, 2002. Color references are made to The Royal Horticultural Society Colour Chart, 1995 Edition, except where general terms of ordinary dictionary significance are used.

Botanical classification: *Alstroemeria hybrida* cultivar Zaprijul.

Parentage:

*Female parent.*—Proprietary *Alstroemeria hybrida* selection identified as 94186-002PN, not patented.

*Male parent.*—Proprietary selection of *Alstroemeria hybrida* identified as 96123-001PN, not patented.

Propagation:

*Type.*—By root divisions.

*Root description.*—Fibrous, fleshy, thick; white, close to 155D, in color.

*Rooting habit.*—Freely branching.

*Rhizomes.*—Shpe: Elongate; rounded. Length: About 10 to 30 cm. Diameter: About 3 to 10 mm. Texture: Smooth. Color: Close to 155D.

Plant description:

*Plant habit.*—Upright, outwardly spreading and compact plant habit; freely branching, about 10 to 15 lateral branches per plant; bushy appearance.

*Time from planting to flowering.*—About 80 to 90 days.

*Plant height.*—About 25 to 35 cm.

*Plant diameter* (*spread*).—About 40 to 50 cm.

*Lateral branch description.*—Aspect: Mostly erect. Length: About 20 to 25 cm. Diameter: About 3 to 5 mm. Internode length: About 5 to 30 mm. Strength: Strong. Texture: Smooth, glabrous. Color: Close to 144B overlain with 60C.

*Foliage description.*—Leaves asymmetrical; sessile. Length: About 6 to 8 cm. Width: About 1 to 2.5 cm. Shape: Lanceolate. Apex: Acute. Base: Attenuate. Margin: Entire. Texture, upper and lower surfaces: Smooth; glabrous. Venation pattern: Parallel. Color: Young and fully developed foliage, upper surface: Close to 137A; slightly glossy. Young and fully developed foliage, lower surface: Close to 137C. Venation: Upper surface: Close to 137A. Lower surface: Close to 137C.

Flower description:

*Flower type and habit.*—Single cup-shaped flowers arranged in compound umbels with about 4 to 16 flowers per umbel. Perianth segments separate. Freely and continuously flowering. Flowers not persistent.

*Natural flowering season.*—Flowering continuous during the spring in The Netherlands.

*Fragrance.*—None detected.

*Keeping quality.*—Plants will stay in flower and maintain good flower substance for about three months.

*Flower longevity on the plant.*—About four weeks.

*Flower longevity as a cut flower.*—About 18 to 20 days.

*Flower buds* (*showing color*).—Length: About 3 to 4.5 cm. Diameter: About 1.2 to 2 cm. Shape: Roughly ovoid. Color: Close to 187A.

*Umbel height.*—About 8 to 12 cm.

*Umbel diameter.*—About 12 to 16 cm.

*Flower diameter.*—About 6 to 8 cm.

*Flower depth.*—About 6 cm.

*Perianth.*—Arrangement: Six arranged in two whorls, each whorl with two lateral and one median segments. Size: Inner perianth: Length: Laterals, about 6.5 to 7 cm; median, 5 to 5.5 cm. Width: Laterals, about 1.5 to 1.8 cm; median, about 1.5 to 2 cm. Outer perianth: Length: Laterals, about 6 to 6.5 cm; median, about 6.5 to 7.5 cm. Width: Laterals, about 3.5 to 4 cm; median, about 3.5 to 4 cm. Shape: Inner perianth, laterals: Lanceolate. Inner perianth, median: Oblanceolate. Outer perianth, all segments: Obovate. Apex: Inner perianth, all segments: Wishbone-shaped. Outer perianth, all segments: Bracket-shaped. Base, inner and outer perianths, all segments: Attenuate. Margin, inner and outer perianths, all segments: Entire; moderately undulate. Texture, inner and outer perianths, all segments: Smooth, glabrous; velvety. Color: Inner perianth, when opening and fully opened, upper surface: Laterals: Towards apex, 70A and 80B; mid-section and base, close to 158B; spots and stripes, close to 187A. Median: Towards apex, 70A and 80B, mid-section and base, close to 155A. Inner perianth, when opening and fully opened, lower surface: Laterals: Towards apex, 70A and 80B; mid-section and base, close to 158B. Median: Towards apex, 70A and 80B; mid-section and base, close to 155A. Outer perianth, when opening and fully opened, upper and lower surfaces, laterals and median: Center, 70A; towards margin, close to 80B; towards base, 155A.

*Pedicels.*—Length: About 1.5 to 2.5 cm. Diameter: About 2 to 3 mm. Strength: Strong. Angle: About 30 to 60° from vertical. Texture: Smooth, glabrous. Color: Close to 144A.

*Reproductive organs.*—Stamens: Quantity per flower: Six. Anther shape: Elliptical. Anther length: About 6 mm. Anther diameter: About 3 mm. Anther color: Close to 191B. Pollen amount: Scarce. Pollen color: Purplish. Pistils: Quantity per flower: One. Style length: About 3.5 to 4 cm. Stigma color: Purple. Ovary color: Close to 144B.

*Fruit.*—Amount: Scarce. Shape: Globular. Color: Brown.

Disease/pest resistance: Plants of the new *Alstroemeria* have not been observed to be resistant to pathogens and pests common to *Alstroemerias.*

Temperature tolerance: Plants of the new *Alstroemeria* have been observed to tolerate temperatures from −5 to 40° C.

It is claimed:

1. A new and distinct cultivar of *Alstroemeria* plant named 'Zaprijul', as illustrated and described.

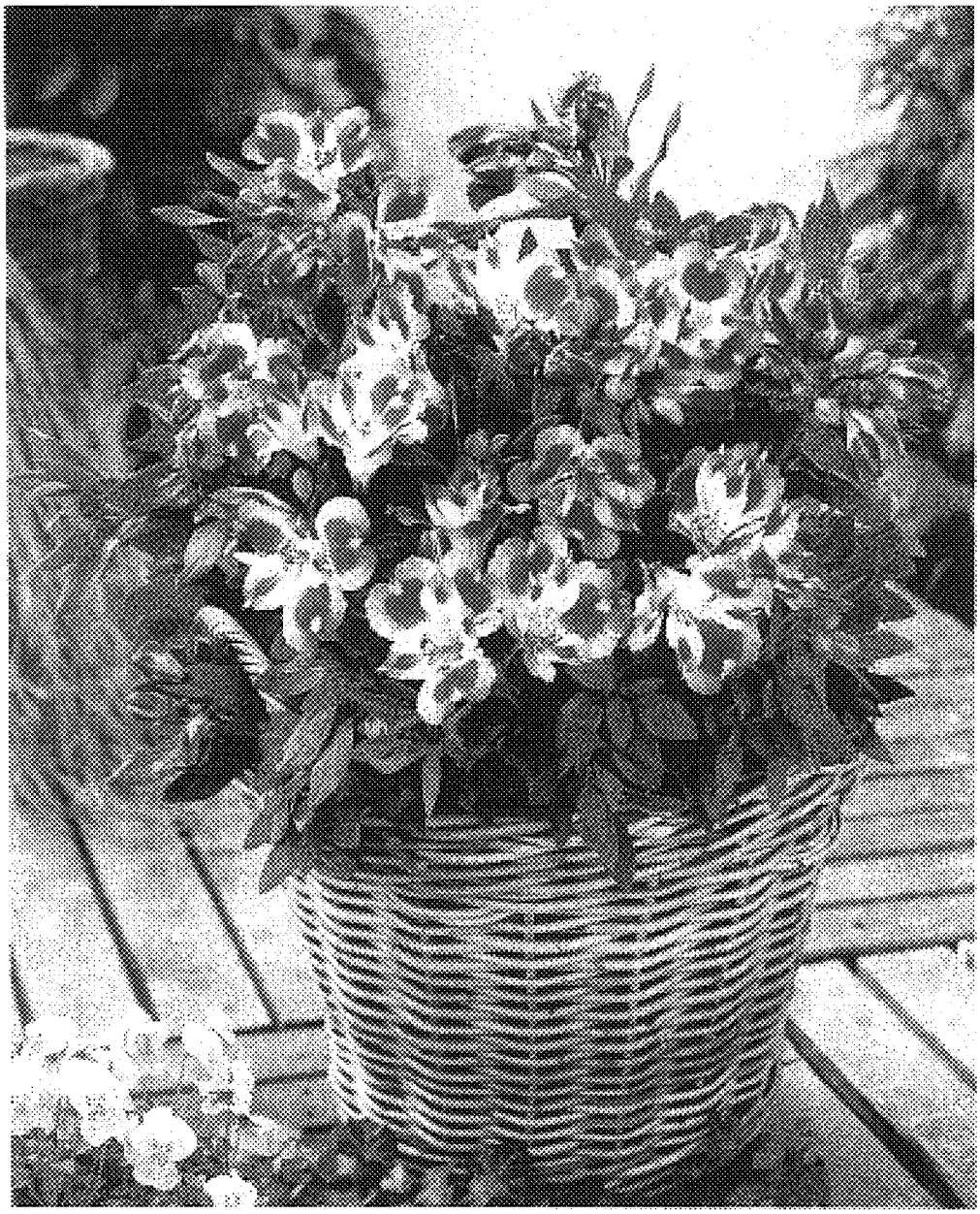

* * * * *